(12) United States Patent
Nardi et al.

(10) Patent No.: US 8,443,678 B2
(45) Date of Patent: May 21, 2013

(54) APPARATUS FOR EVALUATION OF COATED PARTS

(75) Inventors: Aaron T. Nardi, East Granby, CT (US); Blair A. Smith, South Windsor, CT (US)

(73) Assignee: Hamilton Sundstrant Corporation, Windsor Locks, CT (US)

( * ) Notice: Subject to any disclaimer, the term of this patent is extended or adjusted under 35 U.S.C. 154(b) by 0 days.

(21) Appl. No.: 13/438,384

(22) Filed: Apr. 3, 2012

(65) Prior Publication Data

US 2012/0186358 A1    Jul. 26, 2012

Related U.S. Application Data

(62) Division of application No. 12/336,833, filed on Dec. 17, 2008, now Pat. No. 8,177,953.

(51) Int. Cl.
*G01N 3/00* (2006.01)
*G01N 11/00* (2006.01)

(52) U.S. Cl.
USPC .................................. 73/788; 73/760; 73/781

(58) Field of Classification Search
USPC .............................................. 73/788, 760, 781
See application file for complete search history.

(56) References Cited

U.S. PATENT DOCUMENTS

| | | | |
|---|---|---|---|
| 2,670,624 A * | 3/1954 | Faris, Jr. et al. ................. | 374/52 |
| 3,803,485 A | 4/1974 | Crites et al. | |
| 4,033,181 A * | 7/1977 | Oeser .............................. | 73/800 |
| 4,160,702 A | 7/1979 | Baxter | |
| 4,381,663 A | 5/1983 | Swanson | |
| 4,433,582 A * | 2/1984 | Joosten ........................... | 73/788 |
| 4,610,157 A | 9/1986 | Vicki et al. | |
| 4,730,498 A * | 3/1988 | Blanch ............................ | 73/852 |
| 4,764,680 A | 8/1988 | Geary | |
| 4,941,359 A | 7/1990 | Quinn et al. | |
| 5,111,676 A | 5/1992 | Ruzicka, Jr. et al. | |
| 5,142,905 A | 9/1992 | Ezzo et al. | |
| 5,187,987 A * | 2/1993 | Anderson et al. ............... | 73/852 |
| 5,199,305 A | 4/1993 | Smith et al. | |
| 5,277,069 A * | 1/1994 | Cussac et al. ................... | 73/853 |
| 5,500,535 A * | 3/1996 | Jing .......................... | 250/440.11 |
| 5,837,882 A | 11/1998 | Bacigalupo et al. | |
| 5,892,157 A * | 4/1999 | Syre ................................ | 73/812 |
| 6,662,631 B2 | 12/2003 | Baklanov et al. | |
| 7,106,055 B2 | 9/2006 | Goldfine et al. | |
| 7,201,064 B2 * | 4/2007 | Doak et al. ...................... | 73/849 |

(Continued)

OTHER PUBLICATIONS

Variables affecting the fatigue resistance of PVD-coated components, Baragetti, S.; La Vecchia, G.M.; Terranova, A. International Journal of Fatigue, 2005, 1541-1550.

*Primary Examiner* — Lisa Caputo
*Assistant Examiner* — Jamel Williams
(74) *Attorney, Agent, or Firm* — Carlson, Gaskey & Olds

(57) ABSTRACT

A bending test fixture for test coupons includes a test region for receiving a test coupon and first and second supports on opposed sides of the test region. One of the first or second supports includes a first pair of spaced-apart support points and the other of the first or second supports includes a second pair of spaced-apart support points that are narrowly spaced relative to the first pair of spaced-apart support points. There is a load shaft for applying a load to the second support and an articulated joint between the load shaft and the second support for uniformly distributing the load to the first support.

7 Claims, 2 Drawing Sheets

U.S. PATENT DOCUMENTS

| | | |
|---|---|---|
| 7,546,775 B2 * | 6/2009 | Chinavare ..................... 73/849 |
| 2007/0172695 A1 | 7/2007 | Nardi et al. |
| 2007/0256503 A1 * | 11/2007 | Wong et al. ..................... 73/812 |
| 2010/0147694 A1 * | 6/2010 | Nardi et al. ..................... 205/81 |

* cited by examiner

APPARATUS FOR EVALUATION OF COATED PARTS

REFERENCE TO RELATED APPLICATIONS

The present invention is a division of U.S. patent application Ser. No. 12/336,833, filed Dec. 17, 2008 now U.S. Pat. No. 8,177,953.

BACKGROUND OF THE INVENTION

This disclosure relates to a method and fixture for non-destructively verifying performance of a coated part. Hard coatings are typically applied to external surfaces of parts to enhance wear resistance, erosion resistance, or other properties of the part. The hard coating may debit other properties of the part, such as fatigue performance under cyclical loading conditions.

Manufacturers, end-users, or the like may verify fatigue performance of coated parts. For instance, sample parts may be taken from a group of parts and fatigue tested as indication of whether the other parts in the group have a desired level of fatigue performance. One drawback of this methodology is that the tested parts are effectively destroyed in the testing process, which may add expense to the overall manufacturing process.

Another methodology involves indirectly estimating the fatigue performance from a measured property of sample parts or coupons representing sample parts. For instance, coating hardness, modulus of elasticity, or residual stress may be used individually or in combination to estimate a level of expected fatigue performance. The estimation may be based on prior-collected experimental data that establishes a correlation between these properties and fatigue performance. The drawback here is that these properties do not indicate the mechanical strength of the material deposited, but rather a consistency in the plating process which one would suppose would indicate a mechanical strength consistency. Additionally some of these test methods have complexities on their own in how a measurement is made. Additionally, there are questions as to whether these properties are reliable predictors of fatigue performance.

Conventional methodologies for verifying fatigue performance also lack flexibility for variations of the coated parts, such as coating thickness (e.g., different models, part numbers, etc.). For example, a particular hardness, modulus, and residual stress that corresponds to a desired fatigue performance for a coating having a given thickness may not correspond to the desired fatigue performance level if the coating has a different thickness. A new correlation between the coating of the different thickness and the fatigue performance would have to be experimentally established.

SUMMARY OF THE INVENTION

An example bending test fixture for the test coupons includes a test region for receiving the test coupon, and first and second supports on opposed sides of the test region. One of the first or second supports includes a first pair of spaced-apart support points and the other of the first or second supports includes a second pair of spaced-apart support points that are narrowly spaced-apart relative to the first pair. A load shaft applies a load to the first support, and an articulated joint between the load shaft and the first support uniformly distributes the load to the first support.

BRIEF DESCRIPTION OF THE DRAWINGS

The various features and advantages of the disclosed examples will become apparent to those skilled in the art from the following detailed description. The drawings that accompany the detailed description can be briefly described as follows.

DETAILED DESCRIPTION OF THE PREFERRED EMBODIMENT

Figure 1:
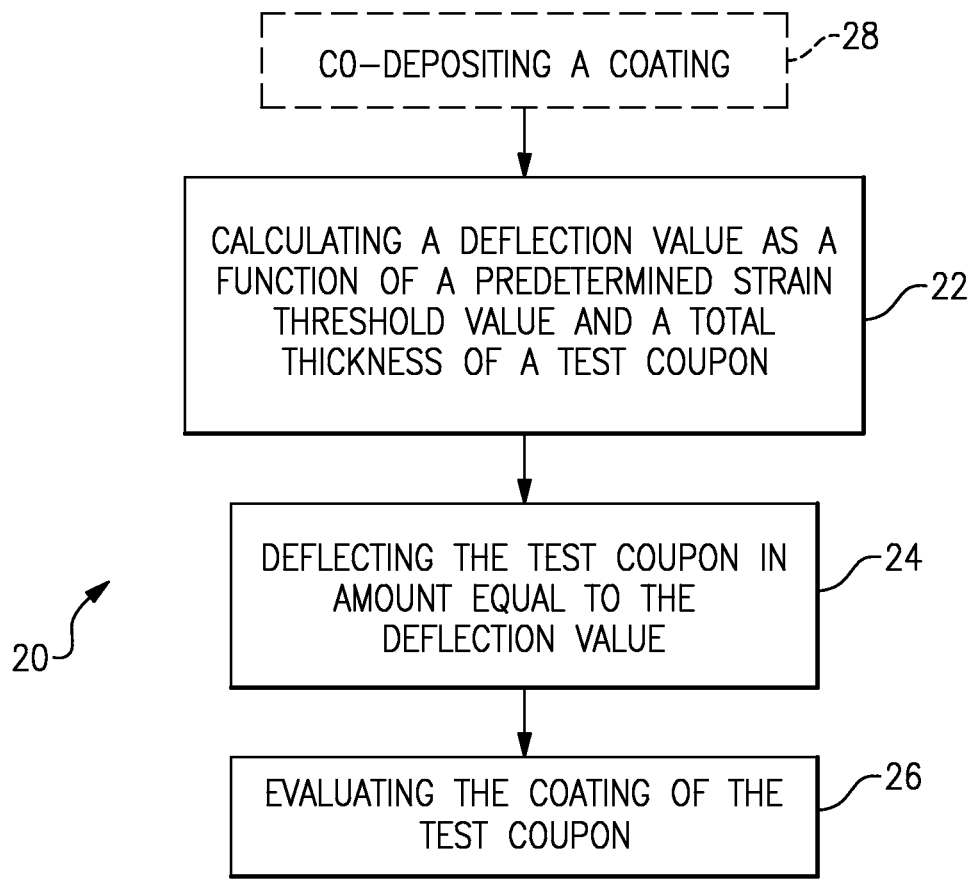
FIG. 1 is an example method of non-destructively verifying performance of a coated part.

FIG. 1 illustrates an example method 20 of non-destructively verifying performance of a coating. It is to be understood that the method 20 is not limited to any particular type of coated part and may be applied parts coated using any deposition process, such as electroplating, plasma-spraying, and the like. In particular, the method 20 involves deflecting a test coupon as an indication of whether a mechanical characteristic, such as fatigue performance, of a coated part meets a specified level. Thus, the method 20 avoids destruction of the coated part or parts for evaluation purposes. The method 20 includes a calculation step 22, a deflection step 24, an evaluation step 26 and, optionally, a co-deposition step 28.

The test coupon may be produced in a co-deposition process such that a substrate of the test coupon and substrate of the part or parts are coated under the same conditions at approximately the same time. The coating of the test coupon is therefore representative of the coating on the coated part. As may be appreciated, the co-deposition step 28 may occur separately from the calculation step 22, deflection step 24, and evaluation step 26, depending on whether a particular manufacturer or other party is responsible for verifying performance of the coated part.

The test coupon may include a generally rectangular steel substrate with the coating deposited on a top surface of the substrate. The steel substrate may be about 25 mm wide, 102 mm long, and 1 mm thick. The coating may be about 0.02-0.2 mm thick, but this disclosure may also be applied to coating thicknesses outside of the example range. In some examples, the substrate may be made of a different material, or may be selected to match the composition of the substrate of the coated parts. Given this description, one of ordinary skill in the art will recognize other suitable geometries for test coupons to meet their particular needs.

The coating may be a hard coating relative to the substrate for providing wear or erosion resistance. For instance, the coating may include cobalt and phosphorous that functions as a protective sheath for the underlying substrate. In some examples, the coating may additionally include hard particulates within a matrix of the cobalt and phosphorous.

A predetermined strain threshold value $\epsilon$ may be used to verify fatigue performance of the coated part using the test coupon. For a particular part geometry and type of coating, the predetermined strain threshold value $\epsilon$ may be known from experimental data, mechanical calculations, or the like. The predetermined strain threshold value $\epsilon$ may be representative of other mechanical characteristics of the parts, such as fatigue performance. That is, a particular specified level of fatigue performance has a corresponding predetermined strain threshold value $\epsilon$. For strains below the predetermined strain threshold value $\epsilon$, the coated part would be expected to meet the specified level of fatigue performance. In other words strain threshold is directly proportional to fatigue performance as both are measuring mechanical performance of the coating rather than a property indicating "coating quality".

The calculation step 22 of method 20 includes calculating a deflection value δ for testing the test coupon to verify whether the coated part meets a desired fatigue performance level. The deflection value δ is a function of the predetermined strain threshold value ε and total thickness (t) of the test coupon, including substrate and coating. An equation for calculating the deflection value δ may be derived based on the geometry of the test coupon, elastic modulii of the coating and substrate, and known mechanical beam equations. For example, the deflection value δ may be calculated using Equation 1 below, where $k_1$ is a first geometry-based constant and $k_2$ is a second geometry-based constant.

$$\delta = \varepsilon(k_1 - k_2 t) \quad \text{(Equation 1)}$$

Equation 1 may be derived from the rectangular geometry of the test coupon and by knowing the elastic modulii of the coating and substrates. Based on this data, the distance from the neutral axis of bending to the centroid of the substrate area may be determined using Equation 2a below, where $w_1$ and $w_2$ respectively represent the effective widths of the substrate and coating of the test coupon and $t_1$ and $t_2$ respectively represent the thicknesses of the substrate and coating of the test coupon. The effective widths are determined by Equation 2b, where $E_1$ and $E_2$ are the modulus of elasticity of the substrate and coating respectively. The distance from the neutral axis of bending to the centroid of the coating area may be determined using Equation 3 below. Equation 4 represents the effective Moment of Inertia, $I_{eff}$, and Equations 5a and 5b represent known equations based on moment-area diagrams, where I is the moment of Inertia, M is the mass and c is the distance from the neutral axis. The combination of equations 2, 3, 4, 5a, and 5b results in the composite Equation 6 below, where $L_1$ and $L_2$ represent the length of the outer and inner bend points of the test fixture and where $E=E_1$ or the modulus of elasticity of the substrate. For a given set of geometric parameters, the deflection value δ may be represented as a function of the predetermined strain threshold value ε and thickness t of the test coupon. The deflection value δ and predetermined strain threshold value ε may then be plotted graphically for various thicknesses t of test coupons to determine the constant $k_1$ and $k_2$.

$$\delta_s = \frac{w_2 t_2}{w_1 t_1 + w_2 t_2}\left(\frac{t_1 + t_2}{2}\right) \quad \text{(Equation 2a)}$$

$$w_2 = \frac{w_1 E_2}{E_1} \quad \text{(Equation 2b)}$$

$$\delta_c = \frac{t_1 + t_2}{2} - \delta_s \quad \text{(Equation 3)}$$

$$\frac{1}{12}w_1 t_1^3 + w_1 t_1 \delta_s^2 + \frac{1}{12}w_2 t_2^3 + w_2 t_2 \delta_c^2 = I_{eff} \quad \text{(Equation 4)}$$

$$\sigma = \frac{Mc}{I} \quad \text{(Equation 5a)}$$

$$\sigma = \varepsilon E \quad \text{(Equation 5b)}$$

-continued $$\delta = \text{deflection} = \left[\frac{4\varepsilon EI}{L_1 - L_2\left(\delta_c + \frac{t_2}{2}\right)} \times \frac{(L_1 - L_2)^3}{48EI}\right] + \left[\frac{4\varepsilon EI}{(L_1 - L_2)\left(\delta_c + \frac{t_2}{2}\right)} \times \frac{L_2(L_1 - L_2)(2L_1 - L_2)}{32EI}\right] \quad \text{(Equation 6)}$$

After calculating the deflection value δ for a given test coupon thickness t, the test coupon is deflected in the deflection step 24 in an amount equal to the calculated deflection value δ. A bending test fixture 42, as will be described below, may be used to deflect the test coupon the calculated amount.

The coating of the test coupon is then evaluated in evaluation step 26 as an indication of whether the fatigue performance, or other mechanical characteristic, of the coated part meets a specified level. For instance, a dye penetrant, such as a fluorescent dye, may be applied to the test coupon after the deflection step 24 to determine whether any cracking has occurred. In some examples, if the test coupon does crack, the cracking may produce an audible noise such that the use of a dye would not be necessary. The occurrence of cracking may indicate that the fatigue performance or other mechanical characteristic of the coated parts do not meet the specified level. Lack of cracking or cracking below a specified amount indicates that the fatigue performance or other mechanical characteristic of the coated parts meets the specified level. In this way the mechanical strength of the coating is directly measured in comparison to a specified value as opposed to parameters which may or may not individually affect the mechanical properties of the coating (i.e. hardness, modulus, residual stress).

Figure 2:
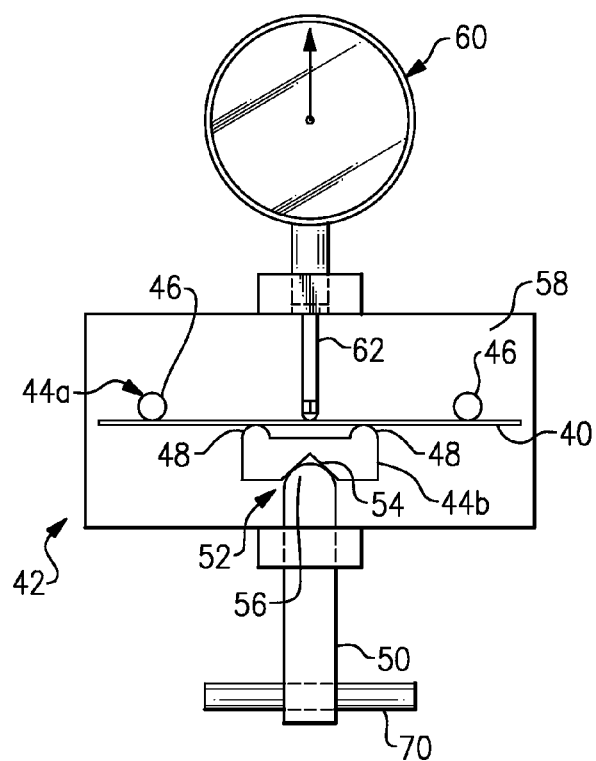
FIG. 2 is an example of a bending test fixture for test coupons.

FIG. 2 illustrates an example bending test fixture 42 (apparatus) for deflecting the test coupon 40 as described above in the deflection step 24 of the method 20. The test coupon 40 generally occupies a test region. The bending test fixture 42 includes first and second supports 44a and 44b on opposed sides of the test region. The first support 44a includes a first pair of spaced-apart support points 46, and the second support 44b includes a second pair of spaced-apart support points 48 that are narrowly spaced relative to the first pair of spaced-apart support points 46. The first pair of spaced-apart support points 46 project from a frame 58.

The spaced-apart support points 46 of the first support 44a contact the test coupon 40 near its ends, and the spaced-apart support points 48 of the second support 44b contact the test coupon 40 near its center. The spaced-apart support points 46 may be about 7.62 cm apart, and the spaced-apart support points 48 may be about 2.54 cm apart. The bending test fixture 42 is therefore adapted for 4-point bending. The bending test fixture 42 distributes the applied load over the area of the test coupon that is between the spaced-apart support points 48. Applying the load over an area of the test coupon avoids concentrating the load on a single point of the test coupon, which could lead to variation in the results of the test.

A load shaft 50 is operably connected to the second support 44b for applying a load to the test coupon 40. It is to be understood that in other examples, the load shaft 50 may alternatively be operably connected to the first support 44a.

The bending test fixture 42 includes an articulated joint 52 between the load shaft 50 and the second support 44b for distributing a load to the second support 44b. That is, there is rotational freedom between the second support 44b and the load shaft 50. For example, the second support 44b includes a socket 54 and the end of the load shaft 50 includes a ball 56 that is received into the socket 54. In this case, the ball 56 is a semi-sphere. Alternatively, the second support 44 may include the ball 56 and the end of the load shaft 50 may include the socket 54.

The socket 54 may have a V-shaped cross-section such that the sides of the ball 56 contact each side of the V-shape when the load is applied. The articulated joint 52 provides the benefit of evenly distributing the load between the spaced-apart support points 48 of the second support 44b to avoid concentrating too much of the load on one point and potentially negatively influencing the outcome of the test.

Figure 3:
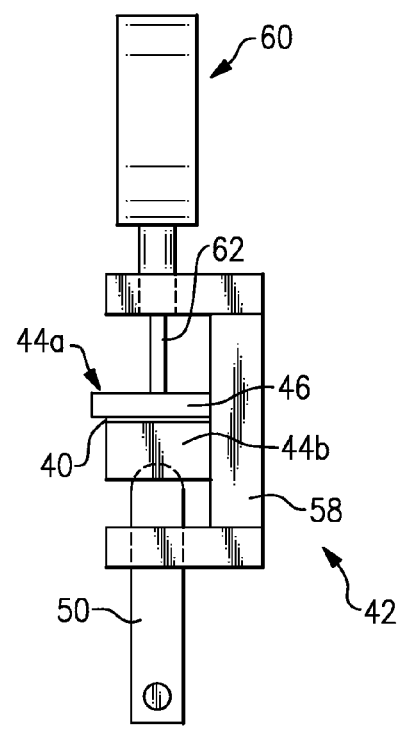
FIG. 3 is an alternate view of the bending test fixture of FIG. 2.

As illustrated in the side view of the bending test fixture 42 of FIG. 3, the first and second supports 44a and 44b, and the load shaft 50 may generally be supported in the frame 58. The frame 58 may also support a gauge 60 having a probe 62 that extends near the test region to detect an amount of deflection of the test coupon 40. In this example, the gauge 60 is a dial indicator that indicates the amount of deflection. However, in other examples, other types of gauges, including electronic gauges, may be used.

Optionally, the bending test fixture 42 may also include a manual crank 70 operably connected with the load shaft 50 for applying a load to the test coupon 40. In operation, a user may apply a load using the manual crank 70 such that the bending test fixture 42 deflects the test coupon 40 to a desired amount that is equal to the calculated deflection value δ. For instance, the user may apply only enough force to result in the desired amount of deflection by watching the gauge and turning the manual crank 70 slowly enough to ramp up the deflection to the desired amount.

A user may utilize the bending test fixture 42 to test one or more test coupons 40 as an indication of whether a fatigue performance of one or more coated parts meets a specified level. That is, if the user applies an amount of deflection equal to the calculated deflection value δ without the test coupon 40 cracking, the parts that were coated along with the test coupons 40 are expected to meet the specified level of fatigue performance. Thus, the test coupons 40 non-destructively verify the performance of the coated part.

Although a combination of features is shown in the illustrated examples, not all of them need to be combined to realize the benefits of various embodiments of this disclosure. In other words, a system designed according to an embodiment of this disclosure will not necessarily include all of the features shown in any one of the Figures or all of the portions schematically shown in the Figures. Moreover, selected features of one example embodiment may be combined with selected features of other example embodiments.

The preceding description is exemplary rather than limiting in nature. Variations and modifications to the disclosed examples may become apparent to those skilled in the art that do not necessarily depart from the essence of this disclosure. The scope of legal protection given to this disclosure can only be determined by studying the following claims.

What is claimed is:

1. A bending test fixture for test coupons, comprising:
a test region for receiving a test coupon;
first and second supports on opposed sides of the test region, wherein one of the first or second supports includes a first pair of spaced-apart support points and the other of the first or second supports includes a second pair of spaced-apart support points that are narrowly spaced relative to the first pair of spaced-apart support points;
a load shaft for applying a load to the second support; and
an articulated joint between the load shaft and the second support for uniformly distributing the load to the first support.

2. The bending test fixture as recited in claim 1, further including a gauge having a probe extending near the test region for detecting an amount of deflection of the test coupon.

3. The bending test fixture as recited in claim 2, wherein the gauge includes a dial indicator for indicating an amount of deflection.

4. The bending test fixture as recited in claim 1, wherein the articulated joint includes rotational freedom between the load shaft and the second support.

5. The bending test fixture as recited in claim 1, wherein one of the second support or the load shaft includes a ball end and the other of the second support or the load shaft includes a socket, the ball end and the socket together forming the articulated joint.

6. The bending test fixture as recited in claim 5, wherein the socket includes a V-shaped cross-section.

7. The bending test fixture as recited in claim 1, further comprising a manual crank operatively connected with the load shaft.

* * * * *

UNITED STATES PATENT AND TRADEMARK OFFICE
CERTIFICATE OF CORRECTION

| | |
|---|---|
| PATENT NO. | : 8,443,678 B2 |
| APPLICATION NO. | : 13/438384 |
| DATED | : May 21, 2013 |
| INVENTOR(S) | : Aaron T. Nardi and Blair A. Smith |

Page 1 of 1

It is certified that error appears in the above-identified patent and that said Letters Patent is hereby corrected as shown below:

On the Title Page:

Item (73) the Assignee should read as follows:

(73) Assignee: Hamilton Sundstrand Corporation
                Windsor Locks, CT (US)

Signed and Sealed this
Seventeenth Day of September, 2013

Teresa Stanek Rea
*Deputy Director of the United States Patent and Trademark Office*